Sept. 19, 1961 E. S. BOERNER Plant Pat. 2,093
ROSE PLANT
Filed Nov. 18, 1960
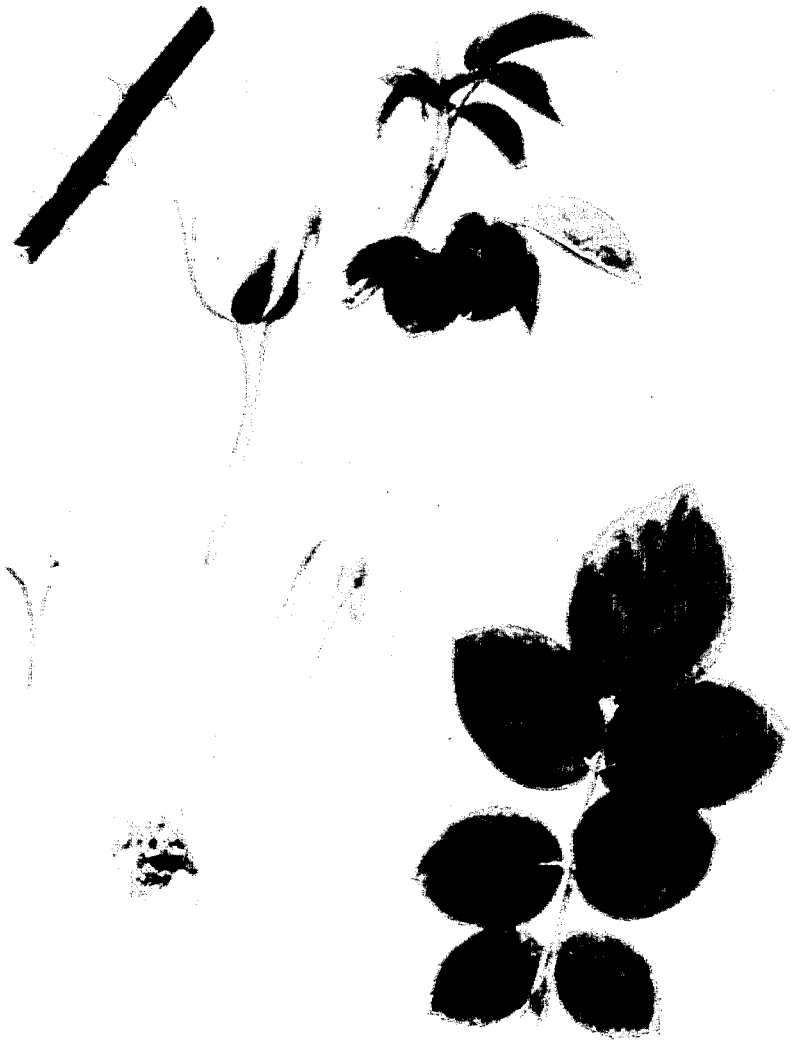
Inventor.
E. S. Boerner
By: Robb & Robb
Attorneys.

United States Patent Office

Plant Pat. 2,093
Patented Sept. 19, 1961

2,093
ROSE PLANT

Eugene S. Boerner, Newark, N.Y., assignor to Jackson & Perkins Company, Newark, N.Y., a corporation of New York Filed Nov. 18, 1960, Ser. No. 70,363
1 Claim. (Cl. 47—61)

The present invention relates to a new and distinct variety of rose plant of the hybrid tea class, which was originated by me by crossing an unnamed and unpatented seedling of the variety "Peace" (Plant Patent No. 591) with the variety "Peace."

The primary objective of this breeding was to produce a new rose variety in which both the plant and flower form of the variety "Peace" is maintained, while at the same time producing more depth of color in the flowers than is present in the regular flowers of the variety "Peace." This objective was fully achieved, as evidenced by the following unique combination of characteristics which are outstanding in the new variety and which distinguish it from its parents, as well as from all other varieties of which I am aware:

(1) A plant habit generally similar to that of the variety "Peace";

(2) An exquisite shape and large size of the flowers; and (3) An unusual and distinctive Ivory Yellow, lightly overcast with La France Pink general tonality of the flowers.

Asexual reproduction of my new variety by budding, as performed at Newark, New York, and also at Pleasanton, California, shows that the aforementioned characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Ridgway's Color Standards and Nomenclature:

Parentage: Seedling.
*Seed parent.*—An unnamed seedling of "Peace."
*Pollen parent.*—"Peace."
Classification:
*Botanic.*—Hybrid tea.
*Commercial.*—Hybrid tea.

*Flower*

(Observations made from specimens grown outdoors at Newark, New York, in the early morning during the latter part of the month of July.)

Blooming habit: Recurrent—continuous.
Bud:
*Size.*—Large.
*Form.*—Ovoid; is not affected by wet or hot weather.
*Color.*—When sepals first divide—Ivory Yellow, Plate 30, with a very light overcast of Shrimp Pink, Plate 1, and with an overcast of Barium Yellow, Plate 16 from the base of the petals. When petals begin to unfurl—Ivory Yellow, Plate 30, lightly overcast with Seashell Pink, Plate 14. When half-blown: inside of petals—Ivory Yellow, Plate 30; reverse of petals—Ivory Yellow, Plate 30, lightly overcast with Shrimp Pink, Plate 1 in the lower half of the petals.
*Sepals.*—Slightly branched; curl back when petals begin to unfurl. Color: inside—Kildare Green, Plate 31; outside—Light Bice Green, Plate 17.

*Calyx.* — Color — Light Bice Green, Plate 17. Shape—funnel. Size—small. Aspect—smooth. Odor when rubbed—none.
*Peduncle.*—Length — medium. Aspect—smooth. Strength—erect; slender. Color—Lettuce Green, Plate 5.
*Opening.*—Opens up well; is not affected by adverse weather conditions.
Bloom:
*Size.*—Very large. Average size when fully expanded—from 5 inches to 5½ inches.
*Borne.*—Singly.
*Stems.*—Medium length; strong.
*Form (when first open).*—Full. Permanence—retains its form to the end.
*Petalage.*—Double (full but open center). Number of petals under normal conditions—from 35 to 40.
*Color.*—Center of flower—Pale Salmon color, Plate 14, lightly overcast with Geranium Pink, Plate 1. Outer petals—Ivory Yellow, Plate 30, faintly overcast with La France Pink, Plate 1 on the outer edges of the petals. Base of petals (aiglet)—Strontian Yellow, Plate 16. Inside of petals—Ivory Yellow, Plate 30, lightly overcast with La France Pink, Plate 1. Reverse of petals—Seashell Pink, Plate 14, lightly overcast with Ivory Yellow, Plate 30. General tonality from a distance—Ivory Yellow, Plate 30, lightly overcast with La France Pink, Plate 1.
*Discoloration.*—General tonality at end of first day—Ivory Yellow, Plate 30, lightly overcast with La France Pink, Plate 1. Second day—Ivory Yellow, Plate 30, lightly overcast with La France Pink, Plate 1. Third day—Ivory Yellow, Plate 30, faintly overcast with La France Pink, Plate 1.
Petals:
*Texture.*—Leathery; is not affected by wet or hot weather.
*Appearance.*—Inside—satiny. Outside—shiny.
*Form.*—Oval; slightly notched.
*Arrangement.*—Imbricated (regularly arranged shingle-like).
*Petaloids in center.*—Few; large.
*Persistence.*—Drop off cleanly.
*Fragrance.*—From moderate to strong. Nature—tea (average hybrid tea scent).
*Lasting quality.*—On the plant—long. As cut flower—long.

*Genital organs*

Stamens, anthers: Large; few; regularly arranged around styles. Color—Apricot Orange, Plate 14.
Stamens, filaments (threads): Medium length. Color—Scarlet Red, Plate 1.
Pollen: Color—Salmon-Buff, Plate 14.
Styles: Bunched; uneven length; medium length; thin.
Stigmas: Color—Coral Red, Plate 13.
Ovaries: Some protruding from calyx.
Hips: None.
Seeds: None.

*Plant*

Form: Bush.
Growth: Vigorous; upright.
Foliage: Compound of 3 to 7 leaflets.
*Size.*—Medium.
*Quantity.*—Normal.
*Color.*—New foliage: upper side—Deep Dull Yellow-Green, Plate 32; under side—Yellowish Oil Green, Plate 5, overcast with Oxblood Red, Plate 1. Old foliage: upper side—Cress Green, Plate 31; under side—Light Cress Green, Plate 31.

*Shape.*—Oval.

*Texture.*—Upper side—leathery. Under side—smooth.

*Ribs and veins.*—Ordinary.

*Edge.*—Serrated (saw-toothed).

*Serration.*—Both double and single; small.

*Leaf stem.*—Color—Kildare Green, Plate 31. Under side—prickly.

*Stipules.*—Medium length; smooth.

Wood:

*New wood.*—Color—Chromium Green, Plate 32. Bark—smooth.

*Old wood.*—Color—Cress Green, Plate 31. Bark—smooth.

Thorns:

*Thorns.*—Quantity: on main stalks from base—ordinary; on laterals from stalk—ordinary. Form—narrow base; short; hooked downward. Color (when young)—Eugenia Red, Plate 13. Position—irregular.

*Prickles.*—Quantity: on main stalks—none; on laterals—none.

*Short needles.*—Quantity: on main stalks—none; on laterals—none.

I claim:

A new and distinct variety of rose plant of the hybrid tea class, substantially as herein shown and described, characterized particularly as to novelty by the unique combination of a plant habit which is generally similar to that of the variety "Peace" (Plant Patent No. 591), an exquisite shape and large size of the flowers comparable to those of the variety "Peace," and an unusual and distinctive Ivory Yellow, lightly overcast with La France Pink general color tonality of the flowers.

No references cited.